(12) United States Patent
Hsu et al.

(10) Patent No.: US 6,275,732 B1
(45) Date of Patent: Aug. 14, 2001

(54) MULTIPLE STAGE MORPHOLOGY-BASED SYSTEM DETECTING VENTRICULAR TACHYCARDIA AND SUPRAVENTRICULAR TACHYCARDIA

(75) Inventors: William Hsu, Circle Pines; Alan F. Marcovecchio, Minneapolis, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 30 days.

(21) Appl. No.: 09/098,654

(22) Filed: Jun. 17, 1998

(51) Int. Cl.[7] .................................................. A61N 1/36
(52) U.S. Cl. .................................................. 607/14
(58) Field of Search ............................... 600/518; 607/14

(56) References Cited

U.S. PATENT DOCUMENTS

| | | | |
|---|---|---|---|
| 4,583,553 | 4/1986 | Shah et al. | 128/704 |
| 4,721,114 | 1/1988 | DuFault et al. | 128/696 |
| 5,000,189 | 3/1991 | Throne et al. | 128/702 |
| 5,014,284 | 5/1991 | Langer et al. | 375/30 |
| 5,014,698 | 5/1991 | Cohen et al. | 128/419 |
| 5,020,540 | 6/1991 | Cahmoun | 128/696 |
| 5,107,850 | 4/1992 | Olive | 128/705 |
| 5,184,615 | 2/1993 | Nappholz et al. | 128/419 PG |
| 5,193,550 | 3/1993 | Duffin | 129/697 |
| 5,215,098 | 6/1993 | Steinhaus et al | 128/702 |
| 5,217,021 | 6/1993 | Steinhaus et al. | 128/702 |
| 5,240,009 | 8/1993 | Williams | 128/702 |
| 5,255,186 | 10/1993 | Steinhaus et al. | 364/413 |
| 5,271,411 | 12/1993 | Ripley et al. | 128/702 |
| 5,275,621 | 1/1994 | Mehra | 607/5 |
| 5,280,792 | 1/1994 | Leong et al. | 128/702 |
| 5,311,874 | 5/1994 | Baumann et al. | 128/705 |
| 5,330,504 | 7/1994 | Somerville et al. | 607/5 |
| 5,331,966 | 7/1994 | Bennett et al. | 128/696 |
| 5,350,406 | * 9/1994 | Nitzsche et al. | 607/14 |
| 5,366,487 | 11/1994 | Adams et al. | 607/5 |
| 5,400,795 | 3/1995 | Murphy etal. | 128/702 |
| 5,447,519 | 9/1995 | Peterson | 607/5 |
| 5,542,430 | 8/1996 | Farrugia et al. | 128/705 |
| 5,645,070 | 7/1997 | Turcott | 128/702 |
| 5,687,737 | 11/1997 | Branham et al. | 128/710 |
| 5,712,801 | 1/1998 | Turcott | 364/550 |
| 5,738,105 | 4/1998 | Kroll | 128/708 |
| 5,772,604 | 6/1998 | Langberg etal. | 600/518 |
| 5,779,645 | 7/1998 | Olson et al. | 600/518 |
| 5,792,065 | 8/1998 | Xue et al. | 600/516 |
| 5,797,399 | 8/1998 | Morris et al. | 128/705 |
| 5,819,007 | 10/1998 | Elghazzawi | 395/51 |
| 5,857,977 | 1/1999 | Caswell et al. | 600/518 |

FOREIGN PATENT DOCUMENTS

| | | | |
|---|---|---|---|
| 0 469 817 A2 | 2/1992 | (EP) | A61N/1/362 |
| 0 506 230 | 9/1992 | (EP) | A61N/1/362 |
| 0711531 | 5/1996 | (EP) | A61B/5/0452 |
| WO 97/39681 | 10/1997 | (WO) | A61B/5/046 |
| 98/53879 | 12/1998 | (WO) | A61N/1/39 |

* cited by examiner

Primary Examiner—William E. Kamm
(74) Attorney, Agent, or Firm—Schwegan, Lundberg, Woessner & Kluth, P.A.

(57) ABSTRACT

A system for detecting ventricular tachycardia and supraventricular tachycardia using a multiple stage morphology based system. Cardiac signals are sensed from a patient's heart and analyzed for the occurrence of a tachycardia event. When a tachycardia event is detected, the method and system analyzes a plurality of features of the sensed cardiac signals in two or more discrimination stages. Each of the two or more discrimination stages classify the tachycardia event as either a ventricular tachycardia or a candidate supraventricular tachycardia event. When a discrimination stage detects the occurrence of a ventricular tachycardia, therapy is delivered to the heart to treat the ventricular tachycardia.

13 Claims, 6 Drawing Sheets

MULTIPLE STAGE MORPHOLOGY-BASED SYSTEM DETECTING VENTRICULAR TACHYCARDIA AND SUPRAVENTRICULAR TACHYCARDIA

FIELD OF THE INVENTION

This invention relates generally to the field of medical devices, and more particularly to a method and system for discriminating and classifying supraventricular tachycardia and ventricular tachycardia events.

BACKGROUND

Recent prospective clinical trials have shown that cardioverter-defibrillators, such as implantable cardioverter-defibrillators (ICDs), reduce sudden arrhythmic death and favorably impact overall mortality in patients at risk for spontaneous ventricular tachyarrhythmia. Cardioverter-defibrillator systems are designed to provide therapy when rapid ventricular activation rates are sensed. However, rapid ventricular rhythms can occur in the presence of a supraventricular tachycardia (SVT). When therapy is applied in response to SVT (in absence of a ventricular tachycardia, VT, or ventricular fibrillation, VF), the therapy is classified as clinically "inappropriate", even though the cardioverter-defibrillator responded appropriately to an elevated ventricular rate.

Cardioverter-defibrillators may deliver inappropriate ventricular therapy to patients afflicted with non-malignant SVTs. These inappropriate therapies may be delivered due to the device's inability to reliably discriminate SVT from malignant VT.

For the reasons stated above, and for other reasons stated below which will become apparent to those skilled in the art upon reading and understanding the present specification, there is a need in the art for a system and a method of reliably and accurately discriminating between the occurrence of a SVT and a VT event during a detected tachyarrhythmia event which can reduce the frequency of inappropriate therapies delivered to cardioverter-defibrillator patients. Such a system may also be suitable for use with patients having implantable cardioverter-defibrillators.

SUMMARY OF THE INVENTION

The present system provides a means for discriminating, or classifying supraventricular tachycardias (SVT) from malignant ventricular tachycardias (VT). The present disclosure teaches a number of embodiments useful for, among other things, classifying a tachycardia or fast arrhythmia as either a SVT or a VT event. In one embodiment, the system utilizes a series of discrimination stages employing a plurality of methods for distinguishing and classifying VT and SVT. In one embodiment, stages are arranged so that the computationally more efficient stages are used initially in assessing and classifying the tachycardia event. In one embodiment, this multiple stage system allows for a more accurate assessment of the patient's condition before treatment is delivered. Furthermore, this multiple stage system allows for earlier (i.e.,faster) treatment of certain VT events, which, in the case of an implantable device, results in a more efficient use of the ICD's battery.

In one embodiment, there is provided a system for classifying VT from SVT during a tachycardia event. Cardiac signals representative of electrical cardiac activity are sensed and analyzed of the occurrence of a tachycardia event. When a tachycardia event is detected, a plurality of features along the sensed cardiac signals are analyzed in two or more discrimination stages. In one embodiment, a discrimination stage is used to distinguish and classify the tachycardia event as either being a VT event or a candidate SVT event.

In one embodiment, the first discrimination stage analyzes the width of repeatably identifiable features on the sensed cardiac signals and compares them to a template value to classify the tachycardia event. In one embodiment, the first discrimination stage acts to measure a width of sensed R-waves using the plurality of features from cardiac signals sensed during a tachycardia event. The width of each of the sensed R-waves is then compared to a template R-wave width. In one embodiment, the template R-wave width is determined from cardiac signals sensed during the patient's normal sinus rhythm.

If the comparison of the sensed R-waves to the template R-wave width reveals that the width of a sensed R-wave is greater than or equal to a predetermined value of the template R-wave width, the cardiac signal is classified as a ventricular tachycardia complex. As the cardiac signals are classified, the number of ventricular tachycardia complexes are recorded, and when the number of ventricular tachycardia complexes reach a predetermined threshold a ventricular tachycardia is declared. Once a ventricular tachycardia is declared, therapy for treating the ventricular tachycardia is delivered to the patient.

If in the first discrimination stage a ventricular tachycardia is not declared, a second discrimination stage is then used to assess and classify the tachycardia event. In one embodiment, the second discrimination stage includes the acts of determining values for each of the plurality of features of the cardiac signals sensed during a tachycardia event. In one embodiment, the plurality of features includes the value of maximum and minimum deflection points along the sensed cardiac signals.

The values for the plurality of features for each of the cardiac signals sensed during the tachycardia event are then used in determining a similarity value and a dissimilarity value. In one embodiment, the similarity value and the dissimilarity value indicate the similarity of the sensed cardiac signal to cardiac signals sensed during normal sinus rhythm. As such, the similarity value and the dissimilarity value for the sensed cardiac complexes are assessed relative to a plurality of features on normal sinus rhythm signals.

The similarity value and the dissimilarity value are then used to determine if each of the cardiac signals is a ventricular tachycardia complex. In one embodiment, this is accomplished by plotting the similarity value and the dissimilarity value on a discrimination plane. Based on where the cardiac signal is plotted on discrimination plane, the cardiac signal is either classified as a ventricular tachycardia complex or a candidate supraventricular tachycardia complex. In one embodiment, the candidate supraventricular tachycardia complex is also known as a non-ventricular tachycardia complex.

As the cardiac signals are classified, the number of ventricular tachycardia complexes are recorded, and when the number of ventricular tachycardia complexes reach a predetermined threshold a ventricular tachycardia is declared. In one embodiment, once a ventricular tachycardia is declared, therapy for treating the ventricular tachycardia is delivered to the patient.

In one embodiment, if in the first discrimination stage the tachycardia event is classified as a candidate supraventricular tachycardia (or a non-ventricular tachycardia) and the second discrimination stage also classifies the tachycardia event as a candidate supraventricular tachycardia, then the tachycardia event is declared a supraventricular tachycardia.

These and other features and advantages of the invention will become apparent from the following description of the embodiments of the invention.

DETAILED DESCRIPTION

Figure 1:
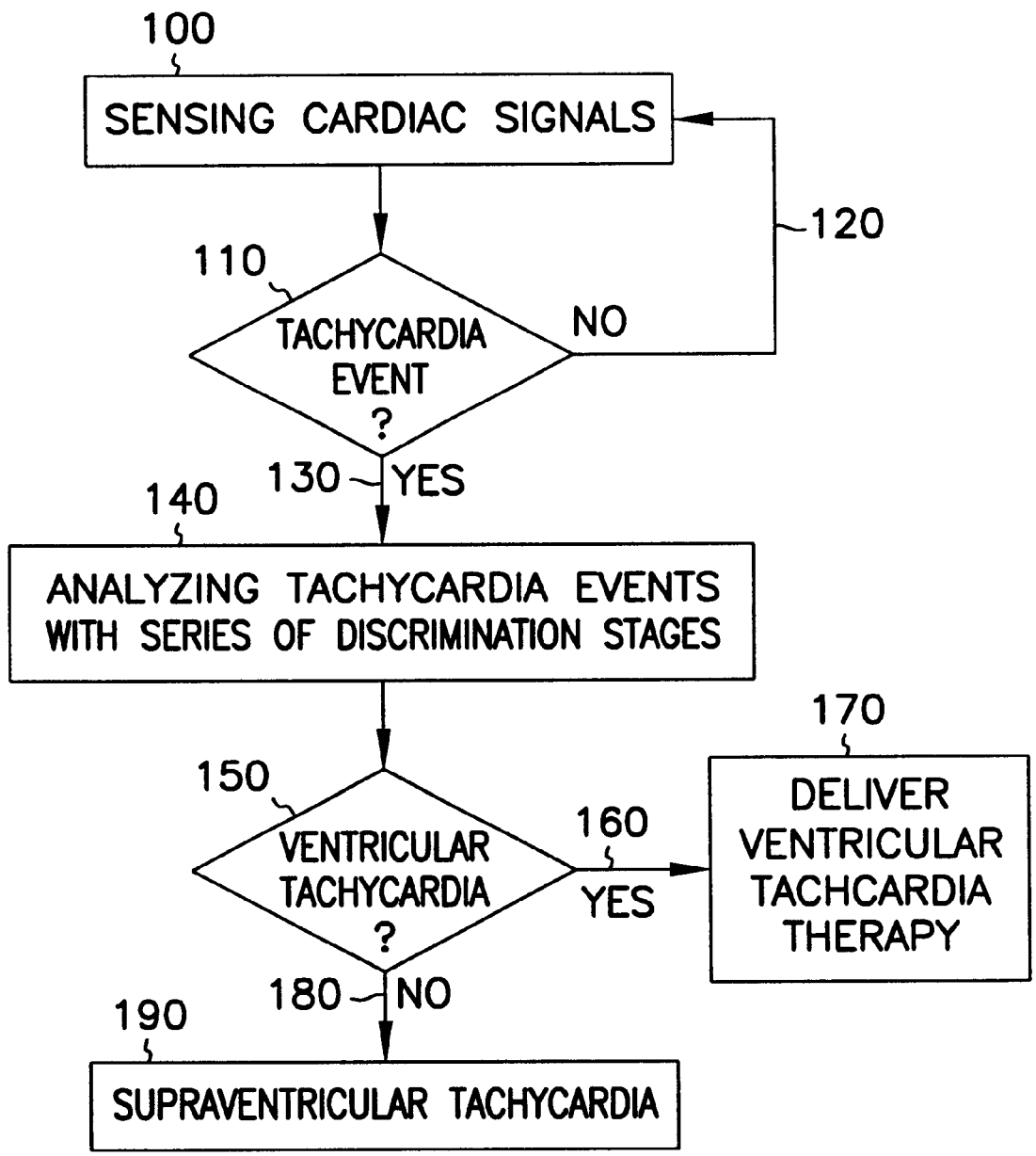
FIG. 1 shows a flow chart illustrating one embodiment of the present system.

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Some of the embodiments illustrated herein are demonstrated in an implantable cardiac defibrillator, which may include numerous defibrillation, pacing, and pulse generating modes known in the art. However, these embodiments are illustrative of some of the applications of the present system, and are not intended in an exhaustive or exclusive sense. For example, the present system is suitable for implementation in a variety of implantable and external devices.

One embodiment of the present system provides a means for discriminating, or classifying, supraventricular tachycardias (SVT) from malignant ventricular tachycardias (VT). The present disclosure provides a number of embodiments useful for, among other things, classifying a tachycardia or fast arrhythmia as either a SVT or a VT. The concepts described herein can be used in a variety of applications which will be readily appreciated by those skilled in the art upon reading and understanding this description. Embodiments of distinguishing of classifying VT and SVT are discussed herein, but other arrhythmic events (both ventricular and supraventricular) can also be distinguished using the teachings provided herein, and therefore, the express teachings of this disclosure are not intended in an exclusive or limiting sense.

In one embodiment, the distinction, or classification, between VT and SVT events is accomplished through the use of a series of discrimination stages which utilize a plurality of methods for distinguishing and classifying VT and SVT. In one embodiment, the series of discrimination stages includes two or more discrimination stages, where each of the two or more discrimination stages classifies the tachycardia event as either a ventricular tachycardia or a candidate supraventricular tachycardia. By using two or more discrimination stages, the present system is able to take advantage of each stage's ability to differentiate between an SVT and a VT event. This series of discrimination stages, therefore, allows for the benefits or advantages of each stage in making the determination between VT and SVT. For example, some stages provide greater sensitivity to correctly classify VT episodes, while other stages allow for greater specificity in classifying SVT episodes correctly. In addition, some stages are more computationally efficient than others, which allows for VT/SVT classification that is accomplished more quickly while using less time and energy resources of the implantable system. Therefore, in one embodiment, the present method and system provides for a synergistic mechanism of making the VT and SVT distinction. This synergistic interaction allows for a more accurate assessment of the patient's cardiac condition which results in more effective treatment being delivered to the patient.

Figure 7:
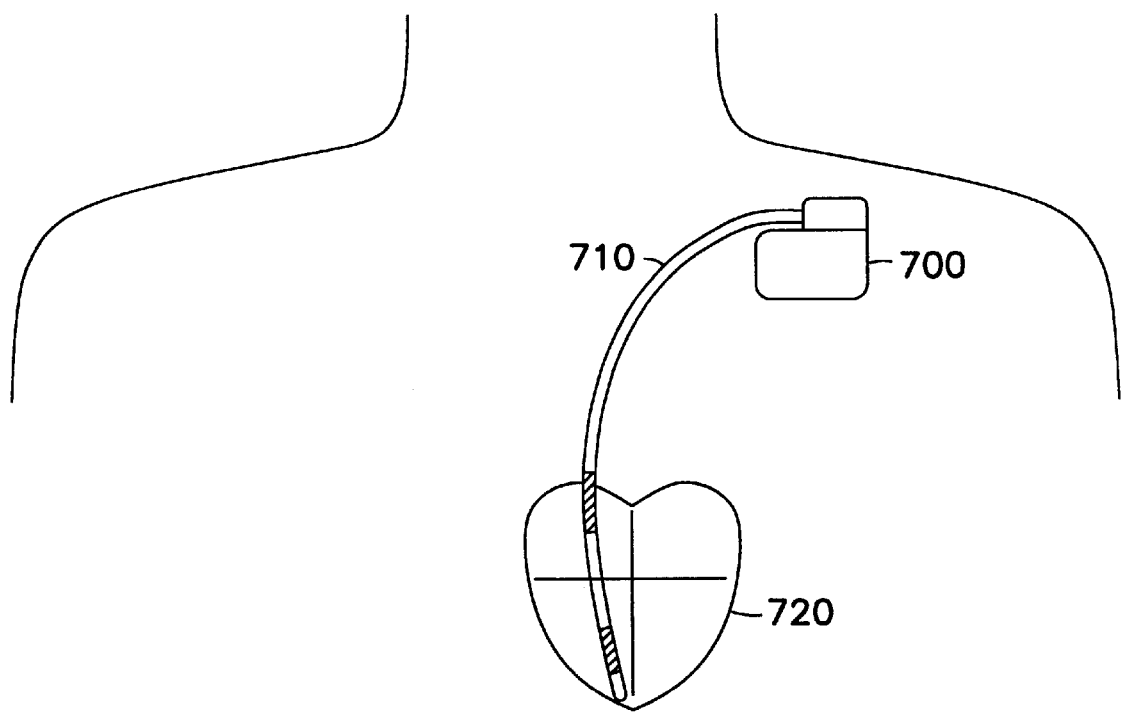
FIG. 7 is a diagram showing an implantable cardioverter-defibrillator and electrodes according to one embodiment of the present system.

A wide variety of methods or stages for distinguishing VT from SVT can be utilized in the present system. In one embodiment, the order in which the stages are applied, or used, affects the accuracy and the speed in making the distinction between VT and SVT. In one embodiment, the system utilizes a series of discrimination stages in which individual stages determine and classify the occurrence of VT and SVT based on sensed cardiac signals. In one embodiment, the sensed cardiac signals are representative of electrical cardiac activity. The embodiments provided herein classify VT from SVT during a tachycardia or fast arrhythmia based on signals sensed by a single chamber implantable cardiac defibrillator. In one embodiment, the single chamber implantable cardiac defibrillator has a multiple electrode, single endocardial lead which senses both ventricular near-field signals (ventricular rate signals) and ventricular far-field signals (ventricular morphology signals). In one embodiment, the implantable cardiac defibrillator employs an single body lead catheter sold under the trademark ENDOTAK (Cardiac Pacemaker, Inc./Guidant Corporation, St. Paul, Minn.) having a pacing tip electrode and two defibrillation coil electrodes. One example of such a system is shown in FIG. 7. ICD 700 is coupled to catheter 710, which is implanted to receive signals from heart 720. The catheter 710 also may be used for transmission of pacing and/or defibrillation signals to the heart 720. In an alternative embodiment, a three defibrillation electrode system is employed, wherein the housing of the implantable system is used as a third defibrillation electrode. In one embodiment, this configuration is known in the art as a "hot can" system.

In an alternative embodiment, a dual chamber implantable cardiac defibrillator is used to classify VT from SVT based on sensed cardiac signals. In one embodiment, the dual chamber implantable cardiac defibrillator includes an ENDOTAK single body lead catheter implanted in the ventricular region of the heart and an atrial catheter implanted in a supraventricular region of the heart. This embodiment allows for ventricular near-field signals and ventricular far-field signals, along with atrial near-field signals to be sensed and analyzed by the implantable cardiac defibrillator.

Other cardiac defibrillator systems and catheter configurations may be used without departing from the present system. In addition to implantable cardiac defibrillator systems, the present system may be utilized in external defibrillation systems and in external cardiac monitoring systems. In addition to employing endocardial leads, the present system can also utilize body surface leads.

Current implantable cardioverter defibrillators frequently deliver inappropriate ventricular therapy to patients afflicted with non-malignant SVTs. These inappropriate therapies are usually delivered due to the device's inability to reliably discriminate SVT from malignant VT during a sensed tachycardia event. Referring to FIG. 1, there is shown one embodiment of a method for classifying VT from SVT during a tachycardia event. At 100, cardiac signals representative of electrical cardiac activity are sensed. In one embodiment, the cardiac signals are sensed by an endocardiac lead system of implantable cardiac defibrillator as previously described. The cardiac signals include cardiac complexes which are portions of the complete cardiac cycles. In one embodiment, the sensed cardiac complexes include the QRS-wave of a cardiac cycle. Included in the QRS-wave is an R-wave, which is produced by the contraction of the ventricle during systole. In one embodiment, the system detects a sensed R-wave for one or more complexes of the cardiac signals sensed by the implantable cardiac defibrillator. At 110, the system analyzes the sensed cardiac complexes to determine if a tachycardia event is occurring. In one embodiment, the system determines the occurrence of a tachycardiac event by analyzing the sensed cardiac rate. A cardiac rate that exceeds a predetermined threshold indicates the occurrence of a ventricular tachycardia. In one embodiment, the predetermined threshold is for cardiac rates of between 150–180 beats per minute. In an alternative embodiment, the predetermined threshold is a lower rate zone of multiple rate-zone device. Other methods of determining the occurrence of tachycardia episode which are known in the art may be used without departing from the present system.

If the system determines that a tachycardia event is not occurring, the system takes path 120 back to 100 and continues to sense and analyze cardiac complexes for the occurrence of a tachycardia event. If a tachycardia event is detected at 110, the system proceeds via 130 to 140. At 140, the cardiac complexes sensed during the tachycardia event are analyzed by a series discrimination stages. In one embodiment, the discrimination stages are procedures which are implemented by an implantable cardiac defibrillator. In one embodiment, the series of discrimination stages are selected in such a way that the discrimination stages progress from stages that are the simplest in terms of implementation (ie., requiring less information or using fewer features extracted from the cardiac complexes and thereby being computationally less complicated) to progressively more complex discrimination stages. In one embodiment, the discrimination stages analyze a plurality of features of the sensed cardiac complexes in two or more discrimination stages, where each of the two or more discrimination stages classifies the tachycardia event as either a ventricular tachycardia or a candidate supraventricular tachycardia.

In one embodiment, the initial stage used at 140 is intended to quickly assess and classify the most easily identifiable tachycardias. In one embodiment, the most easily identifiable tachycardias are those that have cardiac signals with distinctive morphological features which are useful in distinguishing a VT from an SVT episode. In one embodiment, the width of repeatably identifiable features on sensed cardiac complexes are used to distinguish VT from SVT. For example, the width of an R-wave sensed in a QRS-cardiac complex during a tachycardia event is measured and compared to a template R-wave width to distinguish the sensed cardiac complex as either a VT complex or a candidate SVT complex. In one embodiment, when the R-wave width is less than a predetermined value of the template R-wave width, the cardiac signal is classified as a candidate supraventricular tachycardia complex. Additionally, when the R-wave width is greater than or equal to the predetermined value of the template R-wave width, the cardiac signal is classified as a ventricular tachycardia complex. As the cardiac signals are classified, the number of VT complexes and candidate SVT complexes are recorded and analyzed at 150. At 150, when the number of VT complexes exceeds a predetermined threshold, a VT episode is declared. The system then follows path 160 to 170 where therapy is delivered to the patient's heart to treat the VT. Alternatively, when the number of candidate SVT complexes exceed the predetermined threshold, the system then declares a candidate SVT episode and proceeds to the next discrimination stage.

In one embodiment, the next discrimination stage is a more computationally advanced discrimination stage. In one embodiment, the advanced discrimination stage is used on tachycardia events that are more difficult to assess. An example of a tachycardia event that has traditionally been difficult to assess has been narrow complex ventricular tachycardias, or tachycardias with any atrial to ventricular depolarization ratio (including, but not limited to, 1:1).

The number and type of advanced stages used in assessing the tachycardia is a programmable feature of the implantable medical device. In one embodiment, the advanced stages utilize different morphological features from cardiac complexes sensed during the tachycardia event. Based on the morphological features of the cardiac signals, a determination of the origin of the tachycardia event is possible. In an additional embodiment, the advanced stages are weighed in terms of what type of therapy to provide to a patient when two or more advanced stages provide conflicting assessments of the tachycardia event. For example, the system is programmed to deliver therapy based on the determination of a second advanced stage, even though a first advanced stage determination provided an opposing assessment.

As with the initial stages, if at 150 applying series of discrimination stages during the advanced stages results in the determination of a ventricular tachycardiac, the system follows path 160 to 170 where therapy for converting the ventricular tachycardia to normal sinus rhythm is delivered to the patient. Appropriate therapy for treating a ventricular tachycardia can include such therapy as overdrive pacing or delivering cardioversion shocks to the heart. Other types of therapy for treating a ventricular tachycardia are known in the art and considered within the scope of the present system.

At 150, if a ventricular tachycardia is not determined using the series of discrimination stages, the system follows path 180 to 190 where a supraventricular tachycardia is declared. In one embodiment, therapy is delivered to the supraventricular region of the heart to treat the SVT. In an alternative embodiment, therapy is not delivered to the supraventricular region of the heart, but rather the system continues to monitor the cardiac condition and provides treatment only when a ventricular tachycardia is determined.

Figure 2:
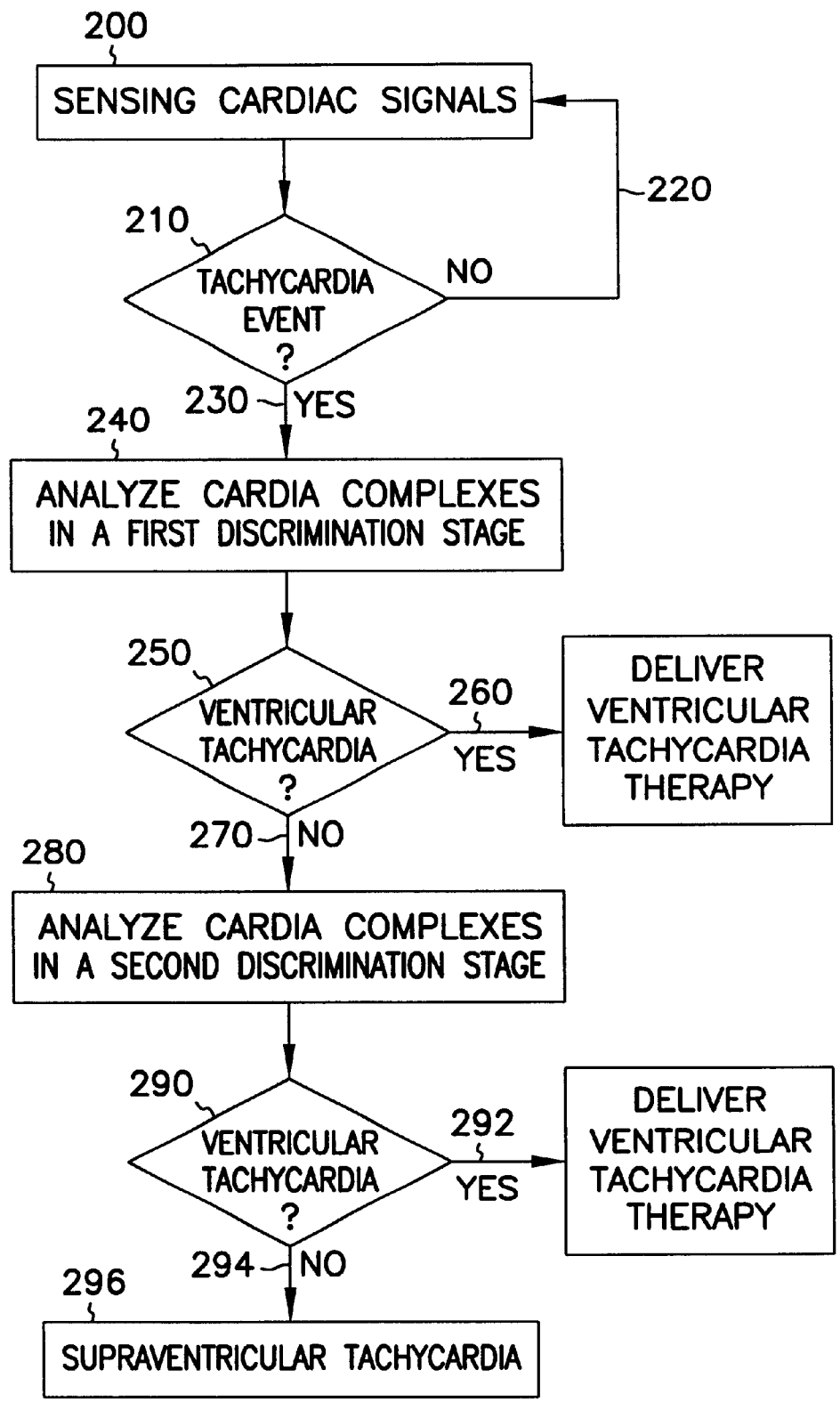
FIG. 2 shows a flow chart illustrating one embodiment of the present system.

Referring now to FIG. 2, there is shown an additional embodiment of the present system for distinguishing the nature of the tachycardia event occurring in the heart. At

200, the system senses cardiac signals representative of electrical cardiac activity. At 210, the system analyzes the sensed cardiac signals to determine if a tachycardia event is occurring. If a tachycardia event is not detected, the system takes path 220 back to 200 and continues to sense and analyze cardiac signals for the occurrence of a tachycardia event or fast arrhythmic event. As previously mentioned, numerous methods, including the use of the cardiac rate, exist in the art for determining the occurrence of tachycardia events, and are considered to be within the scope of the present invention.

If a tachycardia event is detected at 210, the system proceeds along path 230 to 240. At 240 the cardiac signals are analyzed in a first discrimination stage. In one embodiment, the first discrimination stage determines the width of R-waves sensed from the cardiac signals sensed during the tachycardia event. The width of the sensed R-wave is useful in discriminating VT from SVT during a tachycardia event. In one embodiment, the width of the sensed R-waves changes due to differences in the conduction velocity of the hearts intrinsic contraction wave during VT as compared to SVT. During normal sinus rhythm and SVT, electrical stimuli propagate through the His-Purkinje System. This allows for rapid conduction of the electrical stimuli throughout a large portion of the ventricular cardiac tissue. During VT, electrical stimuli must propagate through the myocardium. The conduction velocity in myocardium is less than the conduction velocity in the His-Purkinje System. This difference in conduction velocity often translates into a wider R-wave during VT in both body surface and endocardial biopotentials. This difference allows for cardiac signals to be discriminated and classified by the system.

Figure 3:
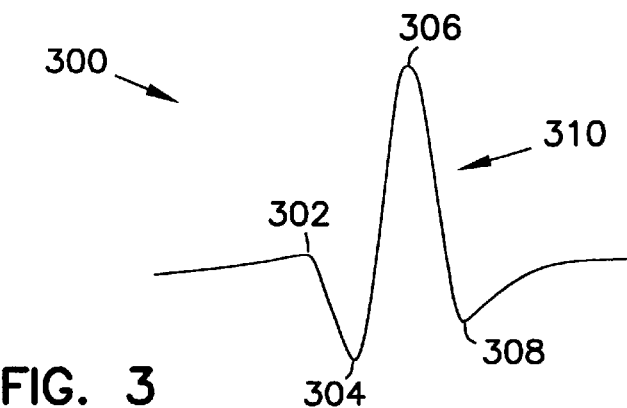
FIG. 3 is a illustration of one example of a sensed cardiac complex.

Referring now to FIG. 3, there is shown one embodiment of a sensed cardiac complex 300. In one embodiment, the sensed cardiac complex 300 is an electrogram recording of the QRS-wave of the cardiac cycle. The sensed cardiac complex 300 displays a plurality of features. In one embodiment, the plurality of features are at major deflection points along the sensed cardiac complex. For example, in FIG. 3 four major deflection points are found at a first feature 302, a second feature 304, a third feature 306, and a fourth feature 308. Values for these major deflection points provide a four element feature vector. In one embodiment, feature vectors are extracted for each tachycardia complex that is sensed. The feature values are then used in measuring the width of the ventricular R-wave 310. In one embodiment, the width of the ventricular R-wave 310 is measured between the second feature 304 at approximately the start of the R-wave 310 and the fourth feature 308 at approximately the end of the R-wave 310.

In one embodiment, the method of classifying VT and SVT by measuring the width of a patient's R-wave 310 involves measuring the width of the R-wave by first digitizing electrical signals from the ventricle to digital signals. The digitized signals are then analyzed to determine the second feature 304 and the fourth feature 308 of the sensed R-waves. The width of the R-wave is then defined as the interval between the second feature 304 associated with a detected R-wave 310 and the fourth feature 308 associated with the same detected R-wave 310.

At 250, the system determines if a ventricular tachycardia is occurring. In one embodiment, the R-wave width is compared to a template R-wave width. In one embodiment, the template R-wave width is an average R-wave width of cardiac complexes sensed during normal sinus rhythm. In an alternative embodiment, the template R-wave width is a median R-wave width of cardiac complexes sensed during normal sinus rhythm. When the R-wave width is greater than or equal to a predetermined value of the template R-wave width, the cardiac complex is categorized as a VT complex. Accordingly, when the R-wave width is less than the predetermined value of the template R-wave width, the cardiac complex is categorized as a candidate SVT complex. In one embodiment, the predetermined value is a programmable value in the range of 20 to 50 percent, where 30 percent is an acceptable value.

As the sensed cardiac complexes are categorized, the system records the number of VT complexes and candidate SVT complexes that have been categorized during the tachycardia event at 250. In one embodiment, the tachycardia event is classified as a VT when the number of VT complexes exceeds a predetermined threshold. In one embodiment, the predetermined threshold is an x out of the last y complexes counter. When x out of the last y complexes are not classified as VT complexes, the system classifies the tachycardia event as a candidate SVT. Candidate SVT events are then analyzed in at least a second discrimination stage to either confirm the presence of an SVT event or determine the presence of a VT event. In one embodiment, the values for x and y are programmable, where x has programmable integer values in the range of 3 to 10, where 5 is an acceptable value, and y has a programmable integer values in the range of 8 to 30, where 10 is an acceptable value. In an alternative embodiment, the system determines a percentage of VT complexes during the tachycardia event. When the percentage of the VT complexes exceeds a predetermined percentage threshold, the system declares the occurrence of a ventricular tachycardia. In one embodiment, the predetermined percentage threshold is a programmable value in the range of 30 to 100 percent, where 50 percent is an acceptable value.

When the number of VT complexes exceeds the predetermined threshold, a VT episode is declared. The system then delivers therapy to the patient's heart to treat the VT event at 260. If a VT episode is not declared, the system records the event as a candidate SVT episode and proceeds along path 270 to the next discrimination stage 280.

In an alternative embodiment, the first arrhythmia discrimination procedures determines changes in the polarity of detected R-waves. The polarity of the detected R-waves is useful in determining VT from SVT. For example, the system records the sign of the largest amplitude of cardiac complexes sensed during normal sinus rhythm. During a tachycardia event, the sign of the cardiac complex feature having the largest amplitude is recorded and compared to that of the normal sinus rhythm. If the largest amplitude feature is different in sign between the normal sinus rhythm an the tachycardia event, the tachycardia event is determined to be a VT event.

At 280, the cardiac signals are analyzed by a second discrimination stage. In one embodiment, the second discrimination stage is either a determination of polarity change in the R-wave or the width of the R-wave, which ever analysis was not utilized in the first discrimination stage. In an alternative embodiment, an advanced procedure is used to assess the tachycardia event. In one embodiment, advanced procedures performs a cardiac complex feature comparison on the sensed cardiac signals. In one embodiment, the cardiac signals feature comparison involves analyzing a morphological similarity of the cardiac signals to a normal sinus rhythm template complex. In one embodiment, analyzing the morphological similarity of the cardiac signals involves determining a similarity feature value and a dissimilarity feature value for each sensed cardiac signals. Based on the calculated feature values, the cardiac signal is classified as either being a ventricular tachycardia complex or a supraventricular tachycardia complex. In one embodiment, the cardiac signal is a far-field or morphology electrocardiogram signal. In an alternative embodiment, the cardiac signal is a near-field or rate electrocardiogram signal.

In one embodiment, when the system proceeds to analyze the tachycardia event in the second discrimination stage, the cardiac signals used in the second discrimination stage are the cardiac signals classified in the first discrimination stage. So in one embodiment, the cardiac signals used in comparing the width of the sensed R-wave to the template R-wave width are the same cardiac signals used in the step of analyzing the morphological similarity of the cardiac signals. This allows the cardiac signals analyzed in the first discrimination stage to be re-evaluated before a decision as to whether the tachycardia is a VT or an SVT. In an alternative embodiment, the cardiac signals classified in the second discrimination stage are different cardiac signals than those classified in the first discrimination stage. So in one embodiment, additional cardiac signals for use in the step of analyzing the morphological similarity of the cardiac signals are sensed by the system.

One example of determination of a similarity feature value and a dissimilarity feature value is discussed in U.S. Pat. No. 5,311,874 by Baumann et al., which is hereby incorporated by reference in its entirety. Values for the similarity feature value and the dissimilarity feature value distinguishes cardiac complexes as either being a ventricular tachycardiac complex or a supraventricular tachycardia complex. This is accomplished through a comparison of a feature vector, A, for a sensed cardiac complex and a feature vector, N, for cardiac complexes sensed during normal sinus rhythm. In one embodiment, the feature vector, A, and the feature vector, N, are four element feature vectors as previously described.

In one embodiment, the feature vector, A, is generated for each cardiac signal sensed during a tachycardia event. In one embodiment, the feature vector, A, is determined from a plurality of features of the cardiac complexes sensed during a tachycardia event. Values for each of the plurality of features are determined by the system. In one embodiment, the morphological features acquired from sensed QRS-waves are used to determine the feature vector, A. The normal sinus rhythm vector, N, is also determined from a plurality of features of the cardiac complexes sensed during normal sinus rhythm. The feature vector, A, is then used with the normal sinus rhythm vector, N, to determine a similarity value and a dissimilarity value for each of the cardiac signals, where the similarity value and the dissimilarity value are assessed relative to a plurality of features on normal sinus rhythm signals.

In one embodiment, feature vectors are derived from morphological features along the sensed cardiac complex waveform. In one embodiment, the morphological features are the extracted amplitude values of peaks and valleys (or maxima and minima) in the QRS wave of each arrhythmic complex through a process called feature extraction. Each arrhythmic complex is isolated according to a known morphological template. In one embodiment, the morphological template operates to detect the activation of an heart beat (such as the occurrence of an R-wave), at which point the electronic control circuitry of the implantable medical device analyzes the complex associated with the signal indicating the activation of the heart beat. In one embodiment, a threshold value or a detection criterion, as known in the art, is used to indicate the activation of the heart beat. The resulting feature vector, A, includes a set of numbers, each number associated with a particular morphological point of the complex.

Each feature vector, A, is then compared with the feature vector, N, representing the patient's QRS complex during normal sinus rhythm. In one embodiment, the feature vector, N, is known as a normal rhythm vector. In one embodiment, the normal rhythm vector, N, is determined from predetermined waveform characteristics of cardiac QRS-waves recorded during normal sinus rhythm. This information is obtained from the normal sinus rhythm snapshot. The resulting normal rhythm vector, N, includes a set of numbers, each number associated with a particular morphological point of the normal sinus rhythm. The electronic control circuitry then compares each feature vector, A, with the normal rhythm vector, N, to calculate a similarity value and a dissimilarity value for each cardiac signal sensed during a tachycardia event.

Figure 4A:
FIG. 4A and FIG. 4B are illustrations of examples of sensed cardiac complexes.
Figure 4B:
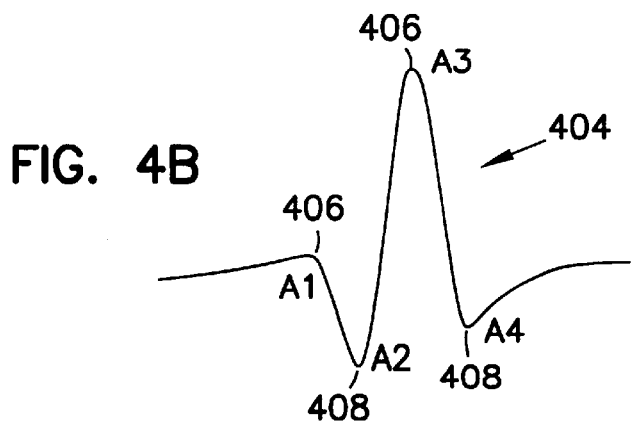

Referring now to FIG. 4A, there is shown one embodiment of an arrhythmic episode electrocardiogram 400. The typical cardiac arrhythmia comprises a series of arrhythmia complexes, or signals, 402(1), 402(2), . . . 402(N) as shown in FIG. 4A. In one embodiment, the implantable medical device 20 determines a similarity value and a dissimilarity value for each of the arrhythmia signals by analyzing the individual QRS waves 404 of the arrhythmic signals relative the patient's normal sinus rhythm. An embodiment of an individual QRS wave 404 is shown in FIG. 4B. The tachycardia complexes are processed by the implantable medical device 20 to determine the amplitudes of peaks 406 and valleys 408 in the QRS complex 404 of the arrhythmia complexes 402(1), 402(2) . . . 402(N). In one embodiment, the peaks 406 and valleys 408 are determined by determining major inflection points in the QRS complex as represented in FIG. 4B.

The resulting values of the peaks 406 and valleys 408 provides a four dimensional feature vector, A=[A1, A2, A3, A4], representing each of the arrhythmic complexes. In one embodiment, the four dimensional feature vector, A, is the four element feature vector used in determining the width of the R-wave. In one embodiment, to align the complexes from different cardiac rhythms, the system 20 is programmed to set the deflection with the largest absolute value as A3. Values for A1 and A2 and A4 are chosen to be the relative extreme immediately before and after A3. If one of the relative extreme does not exist, a slope criterion is used to detect a decrease in slope below a set threshold.

In an additional embodiment, the implantable medical device 20 analyzes the "snapshot" of normal sinus rhythm to determine average amplitudes of peaks and valleys for the QRS complex of the patient's normal sinus rhythm. From these values a four dimensional normal rhythm vector, N=[N1, N2, N3, N4], for normal sinus rhythm is determined. The two vectors A and N are then used to determine values for the similarity and dissimilarity for each tachycardia complex.

Figure 5:
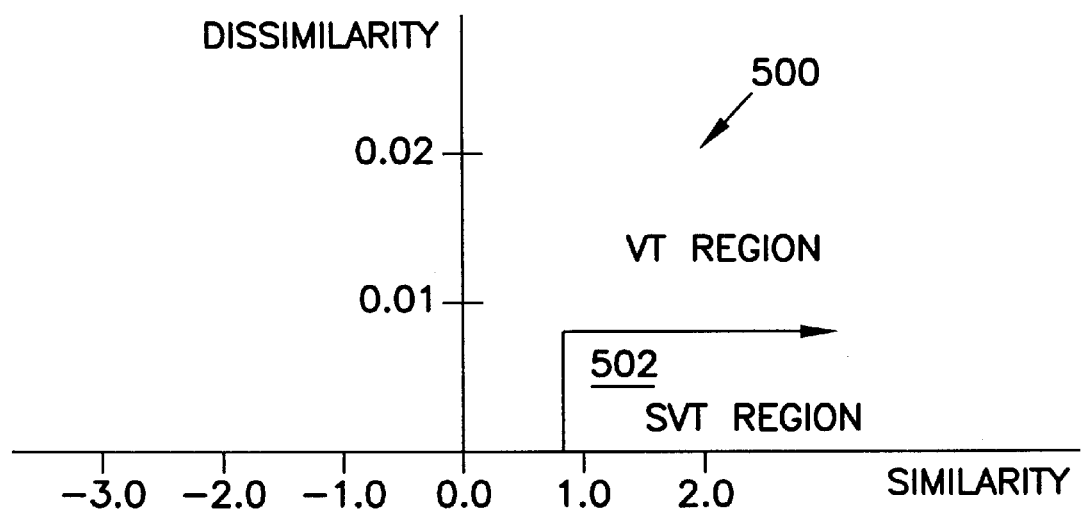
FIG. 5 is an illustration of one example of a similarity/dissimilarity discrimination plane according to one embodiment of the present system.

The similarity feature value and dissimilarity feature value for the tachycardia complex is than mapped onto a discrimination plane 500 as shown in FIG. 5. In one embodiment, a discrimination plane is defined by the two-dimensional plane created by the vectors N/|N| and A/|N|, where the orthogonal axises of the discrimination plane are defined by the similarity feature values (a||) and the dissimilarity feature values (a⊥).

Similarity and dissimilarity feature values are then calculated for the A/|N| vector, where the feature values designated as a∥ and a⊥ are the components of the vector A/|N| parallel and perpendicular, respectively, to the N/|N| vector. The component a∥ represents the degree with which the arrhythmic vector A/|N| is similar to the baseline, or normal, vector N/|N|. This value is obtained by taking the projection (dot product) of the arrhythmic vector A/|N| onto the baseline, or normal, vector N/|N|, which has the units of length. So, the similarity value, a∥, is determined by the equation [A·N]/[N·N]. Thus, the feature value a∥ is the similarity feature of the vector A/|N| with respect to the vector N/|N|. The component a⊥ represents the degree with which the arrhythmic vector A/|N| is dissimilar to the baseline, or normal, vector N/|N|. This value is obtained by taking the projection of the vector A/|N| onto the vector in the discrimination plane which has the unit of length, and which is perpendicular to the vector N/|N|. So, the dissimilarity value, a⊥, is determined by the equation SQRT[(A·A)/(N·N)−(a∥)²]. Thus, the value a⊥, is the dissimilarity feature of the vector A/|N| with respect to the vector N/|N|.

As previously stated the similarity/dissimilarity plane 500 is defined by the two-dimensional plane created by the vectors N/|N| and A/|N|, where the orthogonal axises of the discrimination plane are defined by the similarity feature values (a∥) and the dissimilarity feature values (a⊥). In one embodiment, the similarity/dissimilarity plane is used to classify the arrhythmic episode as a ventricular tachycardia (VT) episodes or a non-VT episodes. FIG. 5, shows the similarity/dissimilarity plane 500 having orthogonal axes a∥ and a⊥, which are referred to as the similarity and dissimilarity coordinate axes.

Next, the location in the discrimination plane of the feature values a∥ and a⊥ for the arrhythmic complex is examined to classify the complex as a VT complex or an SVT complex. Classification of the tachycardia complex is determined by the location of the point, termed the discrimination point, having coordinates equal to the similarity and dissimilarity feature values (a∥ and a⊥) of the arrhythmic complex's vector. If the discrimination point (a∥, a⊥) falls within a predetermined region surrounding the baseline point (1.0,0.0), then the tachycardia complex is classified as a SVT complex. Otherwise, if the discrimination point (a∥ a⊥) falls outside of this region, the tachycardia complex is classified as a VT complex. The boundary separating the non-VT from the VT regions within the discrimination plane is predetermined by testing a population of patients. In one embodiment, the boundary separating the non-VT from the VT regions on the discrimination plane is a fixed boundary and does not change from patient to patient. In an alternative embodiment, the boundary separating the non-VT from the VT regions on the discrimination plane is a programmable boundary that is adapted to a patient's individual medical the therapeutic needs. In addition, the programmable boundary can be programmed with any number of shapes, including, but not limited to rectangular, circle segments, ellipse and ellipse segments, parabolic segments, triangular, parallelogram, or any shape defining an area (whether enclosed on not).

FIG. 5 displays an example of a notice region 502 surrounding the baseline point (1.0, 0.0). In one embodiment, the notice region 502 is defined by the boundary defining the predetermined region. Tachycardia episodes which fall into the notice region 502 are morphologically similar to normal sinus rhythm, but have a cardiac rate that exceeds that of normal sinus rhythm. In one embodiment, tachycardia episodes that fall within notice region 502 are classified as supraventricular tachyarrhythmias. The area falling outside of the notice region 502 is considered to represent ventricular tachycardia activity, and tachycardia complexes falling in this area are considered to represent an ventricular tachycardia arrhythmic episode.

Referring again to FIG. 2, as the sensed cardiac complexes are analyzed at 290, the system records the number of VT complexes and candidate SVT complexes. In one embodiment, the tachycardia event is classified as a VT when the number of VT complexes exceeds the predetermined threshold. In one embodiment, the predetermined threshold is an x out of the last y complexes counter. When the number of VT complexes exceeds the predetermined threshold, a VT episode is declared. The system then delivers therapy to the patient's heart to treat the VT event at 292.

When x out of the last y complexes are not classified as VT complexes, the system classifies the tachycardia event as a candidate SVT. In one embodiment, the values for x and y are programmable, where x has programmable integer values in the range of 3 to 10, where 5 is an acceptable value, and y has a programmable integer values in the range of 8 to 30, where 10 is an acceptable value. In an alternative embodiment, the system determines a percentage of VT complexes and candidate SVT complexes during the tachycardia event. When the percentage of either the VT complexes or the candidate SVT complexes exceeds a predetermined percentage threshold, the system declares the occurrence of the tachycardia that exceeded the predetermined percentage threshold. In one embodiment, the predetermined percentage threshold is a programmable value in the range of 30 to 100 percent, where 50 percent is an acceptable value.

If at 290 the system declares a candidate STV event, so that both the first discrimination stage and the second discrimination stage have declared candidate SVT events, the system follows path 294 and declares an SVT event at 296. In one embodiment, therapy is delivered to the supraventricular region of the heart to treat the SVT. In an alternative embodiment, therapy is not delivered to the supraventricular region of the heart, but rather the system continues to monitor the cardiac condition and provides treatment only when a ventricular tachycardia is determined.

Figure 6:
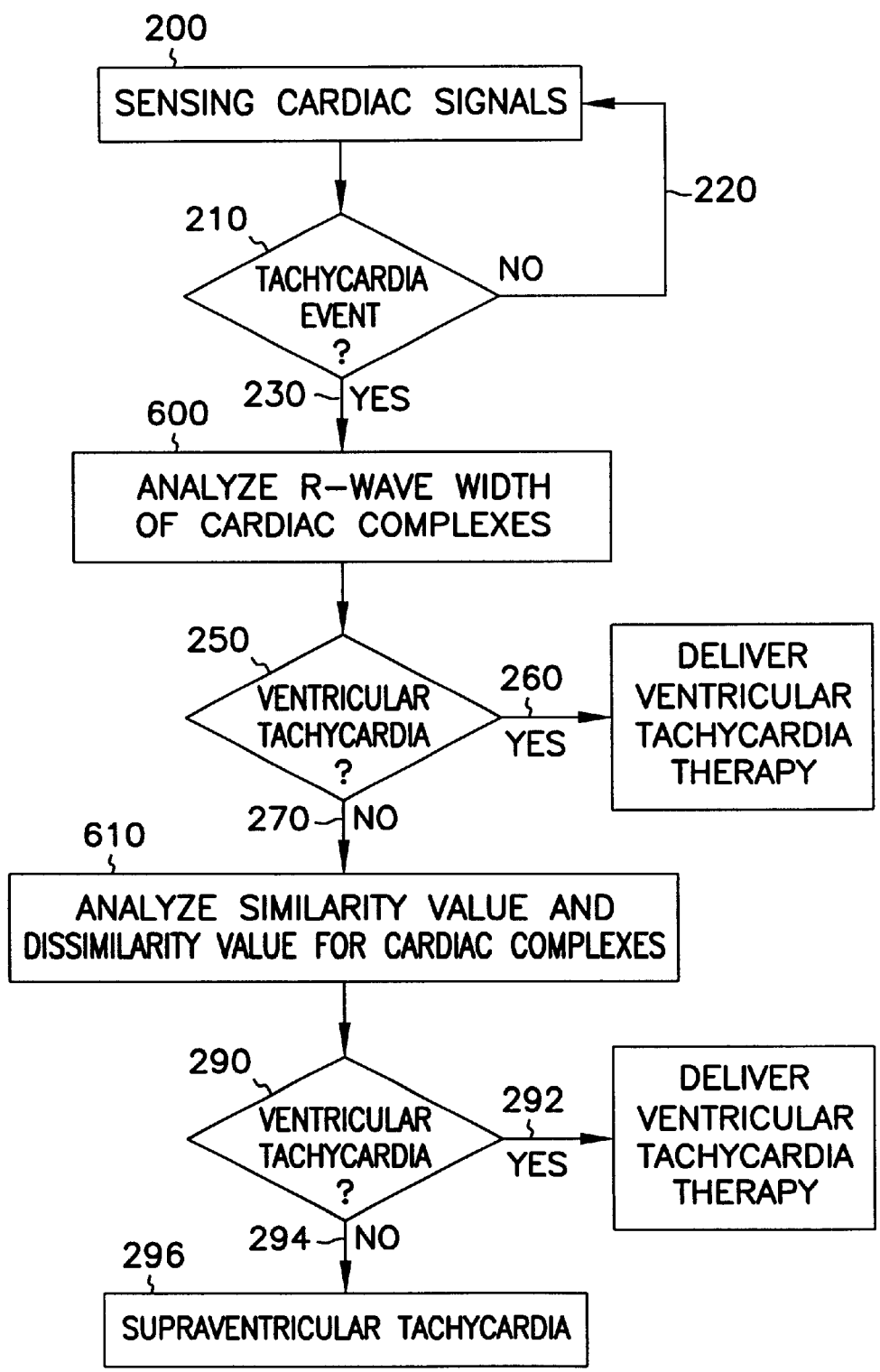
FIG. 6 is one flow diagram demonstrating one embodiment of the present system.

Referring now to FIG. 6, there is shown an additional embodiment of a method for classifying VT from SVT during a tachycardia event. Cardiac signals are sensed at 200 and analyzed at 210 as previously discussed. When a tachycardia event is detected at 210, the system proceeds to 600. At 600, the system analyzes the R-wave width of the sensed cardiac complexes as previously discussed. At 250, if a VT event is not declared, the system then proceeds to 610. At 610, the system determines a similarity value and a dissimilarity value for the cardiac signals sensed during the tachycardia event. Based on the system analysis of the similarity value and the dissimilarity value at 610 for the sensed cardiac signals, the system determines whether a ventricular tachycardia or a candidate supraventricular tachycardia is occurring. Based on the assessment at 290, the system either delivers ventricular tachycardia therapy at 292 or declares a supraventricular tachycardia at 296.

In a further embodiment, additional discrimination stages are added to the system. In one embodiment, a third discrimination stage is added to the series of discrimination stages used in classifying a tachycardia event. The third discrimination stage allows for further assessment and discrimination of VT and candidate SVT events.

The embodiments provided herein are intended to demonstrate only some of the embodiments of the present system. Other embodiments exist which are not described herein and which do not depart from the present system. For example, other stages may be added in varying orders without departing from the present system.

We claim:

1. A method, comprising:

sensing cardiac signals;

analyzing the sensed cardiac signals for a tachycardia event; and during a tachycardia event, analyzing a plurality of features of the sensed cardiac signals in two or more discrimination stages, where each of the two or more discrimination stages classifies the tachycardia event as either a ventricular tachycardia or a candidate supraventricular tachycardia.

2. The method of claim 1, including delivering therapy for treating a ventricular tachycardia when a discrimination stage classifies the tachycardia event as a ventricular tachycardia.

3. The method of claim 1, where the two or more discrimination stages include a first discrimination stage, the first discrimination stage including:

measuring a width of sensed R-waves using the plurality of features from cardiac signals sensed during a tachycardia event;

comparing the width of each of the sensed R-waves to a template R-wave width;

classifying a cardiac signal as a ventricular tachycardia complex if the width of the sensed R-wave is greater than or equal to a predetermined value of the template R-wave width;

declaring a ventricular tachycardia when the number of ventricular tachycardia complexes reach a predetermined threshold; and delivering therapy for treating the ventricular tachycardia when a ventricular tachycardia is declared.

4. The method of claim 3, including:

using a second discrimination stage to classify the cardiac signals, where the second discrimination stage includes:

analyzing a morphological similarity of the cardiac signals to a normal sinus rhythm template complex to determine if a ventricular tachycardia condition is present.

5. The method of claim 4, where analyzing the morphological similarity includes:

determining values for each of the plurality of features of the cardiac signals sensed during a tachycardia event;

determining a similarity value and a dissimilarity value for each of the cardiac signals, where the similarity value and the dissimilarity value are assessed relative to a plurality of features on normal sinus rhythm signals;

using the similarity value and the dissimilarity value to determine if each of the cardiac signals is a ventricular tachycardia complex;

declaring a ventricular tachycardia when the number of ventricular tachycardia complexes reach a predetermined threshold; and delivering therapy for treating the ventricular tachycardia when a ventricular tachycardia is declared.

6. The method of claim 5, wherein the step of using the similarity value and the dissimilarity value include:

defining a boundary on a discrimination plane, where the boundary separates a ventricular tachycardia region from a non-ventricular tachycardia region;

classifying cardiac signals falling in the ventricular tachycardiac region as tachycardia complexes; and classifying cardiac signals falling in the non-ventricular tachycardiac region as supraventricular tachycardia complexes.

7. The method of claim 5, including using the similarity value and the dissimilarity value to determine if each of the cardiac signals is a supraventricular tachycardia complex;

declaring a candidate supraventricular tachycardia when the number of ventricular tachycardia complexes reach a predetermined threshold.

8. The method of claim 7, including the act of declaring a supraventricular tachycardia when both the first discrimination stage and the second discrimination stage declare a candidate supraventricular tachycardia.

9. The method of claim 3, including setting the template R-wave width at an average R-wave width of a plurality of normal sinus rhythm cardiac signals.

10. The method of claim 3, including setting the predetermined value of the template R-wave width between 20 to 50 percent greater than the template R-wave width.

11. The method of claim 3, including classifying the sensed cardiac signal as a candidate supraventricular tachycardia complex if the width of the sensed R-wave is less than the predetermined value of the template R-wave width; and declaring a candidate supraventricular tachycardia when the number of candidate supraventricular tachycardia complexes reach the predetermined threshold.

12. The method of claim 11, where if the cardiac signals classified in the first discrimination stage indicate a candidate supraventricular tachycardia, then analyzing those cardiac signals in the second discrimination stage.

13. The method of claim 11, where if the cardiac signals classified in the first discrimination stage indicate a candidate supraventricular tachycardia, then acquiring further cardiac signals for classification in the second discrimination stage.

* * * * *

UNITED STATES PATENT AND TRADEMARK OFFICE
CERTIFICATE OF CORRECTION

PATENT NO.    : 6,275,732 B1
DATED         : August 14, 2001
INVENTOR(S)   : Hsu et al.

It is certified that error appears in the above-identified patent and that said Letters Patent is hereby corrected as shown below:

<u>Column 11,</u>
Lines 1, 8, 9 and 38, delete "all" and insert -- a$\|$ --, therefor.
Line 11, delete "al" and insert -- a$\perp$ --, therefor.

Signed and Sealed this

Twelfth Day of March, 2002

Attest:

Attesting Officer

JAMES E. ROGAN
Director of the United States Patent and Trademark Office